United States Patent [19]

Vevert et al.

[11] Patent Number: 5,098,934

[45] Date of Patent: Mar. 24, 1992

[54] METHOD OF RELIEVING PAIN WITH MERCAPTOALKANAMIDES

[75] Inventors: Jean-Paul Vevert, Pantin; Francoise Delevallee, Vincennes; Rogert Deraedt, Pavillons sous Bois, all of France

[73] Assignee: Roussel Uclaf, France

[21] Appl. No.: 542,731

[22] Filed: Jun. 22, 1990

Related U.S. Application Data

[63] Continuation of Ser. No. 577,031, Feb. 6, 1984, abandoned.

[30] Foreign Application Priority Data

Feb. 7, 1983 [FR] France .................. 83 01862

[51] Int. Cl.⁵ .............. A61K 31/24; A61K 31/195
[52] U.S. Cl. .................... 514/513; 514/538; 514/539; 514/542; 514/618; 514/625; 558/18; 558/250; 558/253; 558/9; 562/426; 564/162; 564/182; 564/192; 564/209; 564/294
[58] Field of Search .............. 564/162, 192, 209, 214, 564/182; 560/18, 250, 253, 9; 514/513, 538, 539, 542, 618, 625; 558/254; 562/426

[56] References Cited

U.S. PATENT DOCUMENTS

| | | | |
|---|---|---|---|
| 2,184,495 | 12/1941 | Greenacker et al. | 564/192 X |
| 2,535,875 | 12/1951 | Stewart | 564/192 X |
| 2,614,095 | 10/1952 | Shelley, Jr. | 564/192 X |
| 2,709,706 | 5/1955 | Jansen | 260/455 A |
| 2,792,307 | 5/1957 | Chenicek | 564/192 X |
| 3,228,832 | 1/1966 | Margot et al. | 564/192 X |
| 3,590,083 | 6/1971 | Dexter et al. | 564/192 |
| 4,053,651 | 10/1977 | Ondelli et al. | 424/319 |
| 4,055,599 | 10/1977 | Huber-Enden et al. | 564/192 |
| 4,216,160 | 9/1980 | Dorn et al. | 564/192 X |
| 4,248,958 | 2/1981 | Faust | 525/127 X |
| 4,329,495 | 5/1982 | Bindra | 562/426 |
| 4,567,198 | 1/1986 | Dalevallie et al. | 514/513 |
| 4,879,309 | 11/1989 | Doll et al. | 514/513 |

FOREIGN PATENT DOCUMENTS

| | | |
|---|---|---|
| 1989 | 5/1979 | European Pat. Off. |
| 38758 | 10/1981 | European Pat. Off. |
| 100172 | 2/1984 | European Pat. Off. ......... 564/162 |
| 2735178 | 2/1978 | Fed. Rep. of Germany |
| 2009080 | 1/1970 | France |
| 141217 | 12/1978 | Japan ............... 564/192 |
| 472933 | 2/1976 | U.S.S.R. ............ 564/192 |
| 2076809 | 4/1981 | United Kingdom |

OTHER PUBLICATIONS

Kessar et al., Tetrahedron, vol. 24, pp. 899–904 (1968).
Kronberg et al., J. Pharm Sci., vol. 67(5), pp. 595–599 (1978).
Shaikb et al., Bull Chem Soc. Jap., vol. 43, pp. 453–455 (1970).
Vasil'eva et al., CA 99:5168q, 7/1983.
CA 97:5987q.
Jain et al., CA 97: 79862S.
Taliere et al., CA 96: 198929h.
Satsumabayashi et al., CA 95:80997q.
Krouberg et al., CA 89: 99729S.
Szarvasi et al., CA 89: 99734q.
Nacu et al., CA 70: 83943d.
Haejashi et al., CA 68:59672c.
Sirapetyan et al., CA 67:21570j.
Khunyants et al., CA 61: 2966b-g.
Krarasch et al., CA 59:8730e-h.

*Primary Examiner*—Carolyn Elmore
*Attorney, Agent, or Firm*—Bierman and Muserlian

[57] ABSTRACT

Novel ω-mercaptopropanamides and their homologs of the formula

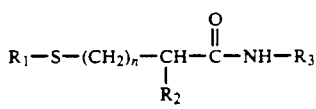

wherein $R_1$ is selected from the group consisting of hydrogen and

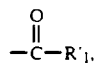

$R_1'$ is selected from the group consisting of alkyl of 1 to 5 carbon atoms and aryl optionally substituted with at least one member of the group consisting of —OH, alkyl and alkoxy of 1 to 5 carbon atoms, —NO$_2$ and halogen, n is an integer from 1 to 5, $R_2$ is selected from the group consisting of hydrogen alkyl of 1 to 5 carbon atoms and aryl and aralkyl of 6 to 15 carbon atoms optionally substituted with at least one member of the group consisting of alkyl and alkoxy of 1 to 5 carbon atoms, —OH, halogen and —CF$_3$, $R_3$ is selected from the group consisting of a) hydrogen, b) phenyl optionally substituted with at least one member of the group consisting of alkyl and alkoxy of 1 to 5 carbon atoms, —OH, —NO$_2$, halogen, —CF$_3$, carboxymethyl, alkoxycarbonylmethyl with 1 to 5 alkoxy carbon atoms, aralkoxy of 7 to 15 carbon atoms and

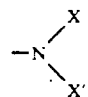

and c) a heterocycle selected from the group consisting of thiazolyl, 4,5-dihydro-thiazolyl, pyridinyl, oxazolyl, isoxazolyl, imidazolyl, pyrimidyl, tetrazolyl, benzimidazolyl, benzothiazolyl and benzoxazolyl, all optionally substituted with alkyl of 1 to 5 carbon atoms, X and X' are individually selected from the group consisting of hydrogen and alkyl of 1 to 5 carbon atoms and their salts with non-taxic, pharmaceutically acceptable acids and bases with the proviso that when $R_2$ is hydrogen and n is 1, $R_3$ is not phenyl optionally substituted with at least one member of the group consisting of halogen and alkyl and alkoxy of 1 to 5 carbon atoms and when $R_2$ is methyl and n is 1, $R_3$ is not phenyl substituted with carboxymethyl having very good analgesic activity and enkephalinase inhibiting activity.

5 Claims, No Drawings

METHOD OF RELIEVING PAIN WITH MERCAPTOALKANAMIDES

PRIOR APPLICATION

This application is a continuation of U.S. patent application Ser. No. 577,031 filed Feb. 6, 1984, now abandoned.

STATE OF THE ART

U.S. Pat. No. 4,053,651 describes certain mercaptoacylamino acids useful for treatment of angiotensin related hypertension and U.S. Pat. No. 4,329,495 describes 2-(2-benzyl-3-mercaptopropionylamino)-1-alkanols and 2-(2-benzyl-3-mercaptopropionylamino)-4-methylthiobutyric acids having enkephalinase inhibition activity. U.S. Pat. No. 4,327,111 describes N-substituted-mercaptopropionamides which inhibit mammalian collagenase. EPO application No. 1,989 describes substituted mercapto acid amides useful to correct an imbalance of immune homeostasis and EPO application No. 38,758 describes amino acid derivatives having analgesic, hypotensive and enkephalinase inhibiting activity.

U.S. Pat. No. 3,770,824 describes N-(4-chlorophenyl)-2-mercapto-acetamide and U.S. Pat. No. 3,878,248 describes N-(3-trifluoromethylphenyl)-2-mercapto-acetamide. U.S. Pat. No. 2,709,706 describes N-phenyl-3-mercapto-propanamide. The said references describe pesticidal, herbicidal or insecticidal activity. Agra. Univ. J. Res. Sci., 1979 (pub. 1981), Vol. 28 (3), p. 139-142 describes N-(2-thiazolyl)-2-mercapto-acetamide as a chemical compound. The above references don't describe any physiological activity for the said compounds.

OBJECTS OF THE INVENTION

It is an object of the invention to provide the novel amides of formula I and their salts with non-toxic, pharmaceutically acceptable acids and bases and a novel method of their preparation.

It is another object of the invention to provide novel analgesic compositions and a novel method of combatting pain in warm-blooded animals.

It is a further object of the invention to provide novel enkephalinase inhibiting compositions and a novel method of inducing enkephalinase inhibiting activity in warm-blooded animals.

These and other objects and advantages of the invention will become obvious from the following detailed description.

THE INVENTION

The novel compounds of the invention are selected from the group consisting of amides of the formula

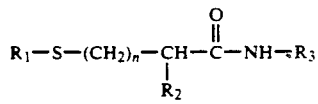

wherein $R_1$ is selected from the group consisting of hydrogen and

$R_1'$ is selcted from the group consisting of alkyl of 1 to 5 carbon atoms and aryl optionally substituted with at least one member of the group consisting of —OH, alkyl and alkoxy of 1 to 5 carbon atoms, —$NO_2$ and halogen, n is an integer from 1 to 5, $R_2$ is selected from the group consisting of hydrogen, alkyl of 1 to 5 carbon atoms and aryl and aralkyl of 6 to 15 carbon atoms optionally substituted with at least one member of the group consisting of alkyl and alkoxy of 1 to 5 carbon atoms, —OH, halogen and —$CF_3$, $R_3$ is selected from the group consisting of a) hydrogen, b) phenyl optionally substituted with at least one member of the group consisting of alkyl and alkoxy of 1 to 5 carbon atoms, —OH, —$NO_2$, halogen, —$CF_3$, carboxymethyl, alkoxycarbonylmethyl with 1 to 5 alkoxy carbon atoms, aralkoxy of 7 to 15 carbon atoms and

and c) a heterocycle selected from the group consisting of thiazolyl, 4,5-dihydro-thiazoyl, pyridinyl, oxazolyl, isoazolyl, imidazolyl, pyrimidyl, tetrazolyl, benzimidazolyl, benzothiazolyl and benzoxazolyl, all optionally substituted with alkyl of 1 to 5 carbon atoms, X and X' are individually selected from the group consisting of hydrogen and alkyl of 1 to 5 carbon atoms and their salts with non-toxic, pharmaceutically acceptable acids and bases with the proviso that when $R_2$ is hydrogen and n is 1, $R_3$ is not phenyl optionally substituted with at least one member of the group consisting of halogen and alkyl and alkoxy of 1 to 5 carbon atoms and when $R_2$ is methyl and n is 1, $R_3$ is not phenyl substituted with carboxymethyl.

When $R_1$ is

$R_1'$ is preferably methyl or ethyl and when $R_1'$ is aryl, it is preferably phenyl and when $R_1'$ is substituted aryl, the substituents are preferably selected from the group consisting of —OH, methyl, ethyl, methoxy, ethoxy, —$NO_2$ and —Cl, n is preferably 1 or 2.

When $R_2$ is alkyl, it is preferably methyl, ethyl, n-propyl, isopropyl, n-butyl, isobutyl or n-pentyl and when $R_2$ is aryl or aralkyl it is preferably phenyl, benzyl or phenethyl. When $R_2$ is substituted aryl or aralkyl, the substituents are preferably selected from the group consisting of methyl, ethyl, methoxy, ethoxy, —OH, —Cl and —$CF_3$.

When $R_3$ is heterocycle substituted with alkyl, the alkyl is preferably methyl or ethyl and when $R_3$ is a substituted phenyl, the substituent is preferably at least one member of the group consisting of —OH, methyl, ethyl, methoxy, ethoxy, —$CF_3$, —$NO_2$, —Cl, —$NH_2$ and

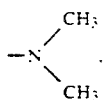

carboxymethyl, benzyloxy and alkoxycarbonylmethyl.

Examples of suitable non-toxic, pharmaceutically acceptable acids are inorganic acids such as hydrochloric acid, hydrobromic acid, nitric acid, sulfuric acid and phosphoric acid and organic acids such as acetic acid, formic acid, propionic acid, benzoic acid, maleic acid, fumaric acid, succinic acid, tartaric acid, citric acid, oxalic acid, glyoxylic acid, aspartic acid, alkane sulfonic acids such as methane sulfonic acid or ethane sulfonic acid, aryl sulfonic acids such as benzene sulfonic acid and p-toluene sulfonic acid and arylcarboxylic acids.

Examples of suitable salts formed with non-toxic, pharmaceutically acceptable bases are alkali metal salts such as those formed with sodium and potassium and amine salts such as those formed with trimethylamine or dimethylamine.

Among the preferred compounds of formula I are those wherein $R_1$ is hydrogen or acetyl, those wherein $R_2$ is not hydrogen and especially those wherein n is 1 and $R_2$ is benzyl and those wherein $R_3$ is pyridinyl or phenyl optionally substituted with at least one chlorine or at least one methoxy and their salts with non-toxic, pharmaceutically acceptable acids and bases.

Specific preferred compounds of the invention are selected from the group consisting of α-(mercaptomethyl)-N-phenyl-benzenepropanamide, ethanethioate of S-[3-oxo-3-phenylamino-2-benzylpropyl], α-(mercaptomethyl)-N-(3-methoxyphenyl)-benzene-propanamide, α-(mercaptomethyl)-N-(4-methoxyphenyl)-benzene-propanamide, α-(mercaptomethyl)-N-(4-pyridinyl)-benzene-propanamide and their addition salts with non-toxic, pharmaceutically acceptable acids and bases.

The novel process of the invention for the preparation of the compounds of formula I wherein n is 1 comprises reacting an acid of the formula

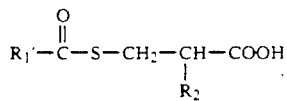

or a functional derivative thereof wherein $R_1'$ and $R_2$ have the above definitions with a compound of the formula $$H_2-N-R_3 \qquad III$$

wherein $R_3$ has the above definition to obtain a compound of formula I wherein $R_1$ is

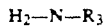

and $R_1'$, $R_2$ and $R_3$ have the above definition and n is 1 and optionally saponifying the latter to obtain the corresponding compound of formula I wherein $R_1$ is hydrogen. The said compounds may be reacted with an acid or base to form the salt thereof.

A process for the preparation of compounds of formula I wherein $R_1$, $R_2$ and $R_3$ have the above definitions and n is 1 to 5 comprises reacting an acid of the formula $$X_1-(CH_2)_n-CH-COOH \qquad IV$$
$$\quad\quad\quad\quad\quad\quad |$$
$$\quad\quad\quad\quad\quad\quad R_2$$

wherein $X_1$ is halogen and n and $R_2$ have the above definitions with a compound of formula III to obtain a compound of the formula

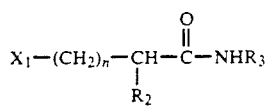

reacting the latter with an anion of a thioacid of the formula $$\begin{array}{c} O \\ \parallel \\ R_1'-CSH \end{array} \qquad VI$$

wherein $R_1'$ has the above definition to obtain a compound of formula I wherein $R_1$ is

n is 1 to 5 and $R_1'$, $R_2$ and $R_3$ have the above definitions which can be saponified to obtain a compound of formula I wherein $R_1$ is hydrogen. The compounds of formula I may be reacted with an acid or base to form the salts thereof.

In a preferred embodiment of the process, the functional derivative of the acid of formula II is the acid chloride and $X_1$ in the compounds of formula IV is preferably chlorine. The condensation of the compounds of formula II or IV with the amine of formula III is preferably effected in a solvent such as ether, tetrahydrofuran, a chlorinated solvent such as methylene chloride, 1,1-dichloroethane, chloroform or carbon tetrachloride or a ketone such as acetone or methylethylketone.

The novel analgesic and enkephalinase inhibiting compositions of the invention are comprised of an analgesically and enkephalinase inhibitory effective amount of at least one compound of formula I and their salts with non-toxic, pharmaceutically acceptable acids and bases and an inert pharmaceutical carrier or excipient. The compositions may be in the form of tablets, dragees, gelules, granules, suppositories, pomades, creams, gels, injectable solutions or suspensions or aerosols.

Examples of suitable excipients are talc, arabic gum, lactose, starch, magnesium stearate, cacao butter, aqueous and non-aqueous vehicles, fatty bodies of animal or vegetable origin, paraffinic derivatives, glycols, diverse wetting agents, dispersants or emulsifiers and preservatives.

Among the preferred compositions of the invention are those wherein the active compound is selected from the group consisting of α-(mercaptomethyl)-N-phenyl-benzene-propanamide, ethanethioate of S-[3-oxo-3-phenylamino-2-benzyl-propyl], α-(mercaptomethyl)-N-(3-methoxyphenyl)-benzene-propanamide, α-(mercaptomethyl)-N-(4-methoxyphenyl)-benzene-propanamide, α-(mercaptomethyl)-N-(4-pyridinyl)-benzene-propanamide and their salts with non-toxic, pharmaceutically acceptable acid addition salts.

Enkephalinase is a dipeptidylcarboxy-peptidase which specially hydrolyses methionine and leucine enkephaline between the third and fourth amino acids liberating a tripeptide Tyr-Gly-Gly [Swerts et al, Europ. J. Pharmacol., Vol. 57 (1979), p. 279]. Enkephalinase directly participates as well in the physiological degradation of enkephalines, natural endogenic ligands to opiaced receptors. The compositions of the invention which retard the degradation of enkephalines stimulate the defense reactions of the organism against pain.

The compositions are useful for the treatment of muscular, articular or nervous pain, rhumatismal affections, dental pain, zonas and migraines as well as the treatment of inflammatory conditions, especially arthrosis, lumbagos and as a complementary treatment in infectious or feverish states.

The novel method of the invention for treating pain and inducing enkephalinase inhibiting activity in warm-blooded animals, including humans, comprises administering to warm-blooded animals an analgesically and enkephalinase inhibiting effective amount of at least one compound of formula I and their salts with non-toxic, pharmaceutically acceptable acids and bases. The compounds may be administered orally, rectally, parenterally or by topical application to the skin and mucous. The usual daily dose is dependent on the compound, the method of administration and the condition being treated. For example, an oral administration consists of 0.25 to 25 mg/kg per day.

Some of the compounds of formulae II and IV are described in U.S. Pat. No. 4,053,651 or may be prepared by the process described therein or is described herein. The compounds of formula V are novel and are an object of the invention.

In the following examples there are described several preferred embodiments to illustrate the invention. However, it is to be understood that the invention is not intended to be limited to the specific embodiments.

EXAMPLE 1

Ethanethioate of
S-[3-oxo-3-phenylamino-2-benzyl-propyl]

STEP A: α-acetylthiomethyl-benzene-propanoyl chloride

A solution of 1.21 g of α-benzyl-acrylic acid [described by Mannich et al, Chem. Ber., Vol. 57B (1924), p. 1116-8] in 0.8 g of thioacetic acid was held under argon at room temperature for one hour and was heated at 100° C. for one hour. Excess thioacetic acid was distilled under reduced pressure and 1.8 g of thionyl chloride was added dropwise with stirring under argon at 0° C. to the oil residue. The mixture was held overnight at room temperature and excess thionyl chloride was evaporated under reduced pressure. 50 ml of benzene were added to the residue and was evaporated under reduced pressure. The oil residue was distilled to obtain 1.87 g of α-acetylthiomethyl-benzene-propanoyl chloride with a boiling point of 150° C. at $10^{-2}$ Torr.

STEP B: Ethanethioate of S-[3-oxo-3-phenylamino-2-benzyl-propyl]

A solution of 4.2 g of aniline in 250 ml of dichloromethane was added at −35° C. under argon to a solution of 16 g of the product of Step A in 250 ml of dichloromethane and the mixture was stirred overnight at room temperature and was filtered to remove aniline hydrochloride. The filtrate was washed with 0.1N hydrochloric acid and then with water until the wash water was neutral. The filtrate was dried and evaporated to dryness. The 21 g of residue were added to a mixture of 100 ml of pentane and 50 ml of ether and the mixture was vacuum filtered. The product was dried under reduced pressure to obtain 16 g of ethanethioate of S-(3-oxo-3-phenylamino-2-benzyl-propyl] melting at 110° C.

EXAMPLE 2

α-mercaptomethyl-N-phenyl-benzene propanamide 20 ml of N sodium hydroxide were added to 5° to 10° C. to a solution of 6 g of the product of Example 1 in 100 ml of methanol and the mixture was stirred at room temperature for 7½ hours. The methanol was evaporated under reduced pressure and the mixture was filtered. The filtrate was acidified with N hydrochloric acid and was extracted with dichloromethane. 3.5 g of oil residue were chormatographed over silica gel and was eluted with a 1-1 pentane-ether mixture to obtain 2.8 g of raw product. The latter was triturated with pentane, filtered and dried under reduced pressure to obtain 2.4 g of α-mercaptomethyl-N-phenylbenzene-propanamide melting at 70° C.

EXAMPLE 3

Ethanethioate of
S-[3-(4-chlorophenylamino)-3-oxo-2-benzylpropyl]

A solution of 8.05 g of 4-chloro-aniline in 150 ml of dichloromethane was added dropwise with stirring under argon at −35° C. to a solution of 8 g of the product of Step A of Example 1 in 100 ml of dichloromethane and the temperature returned to 20° C. The mixture was stirred for 64 hours and was filtered to remove 4-chloroaniline hydrochloride. The filtrate was washed with 0.1N hydrochloric acid, then with water, was dried and evaporated to dryness. The 10.6 g of residue was triturated with 150 ml of a 1-2 pentane-ether mixture, was filtered and dried under reduced pressure to obtain 6.9 g of ethanethioate of S-[3-(4-chlorophenylamino)-3-oxo-2-benzyl-propyl] melting at 130° C.

EXAMPLE 4

N-(4-chlorophenyl)-α-mercaptomethyl-benzene-propanamide 33 ml of sodium hydroxide solution were added under argon over 30 minutes at 5° C. to a solution of 11.2 g of the product of Example 3 in 300 ml of methanol and the mixture was stirred at 15° C. for 2 hours and was cooled to 2° C. The pH was adjusted to 7 by addition of N hydrochloric acid and 200 ml of iced water were added thereto. The mixture was vacuum filtered and the crystals were washed with water and dried under reduced pressure. The 8.9 g of residue were chromatographed over silica gel and was eluted with a 1-1 hexane-dichloromethane mixture. The 6.4 g of product were triturated in pentane, filtered and dried under reduced pressure to obtain 6.2 g of N-(4-chlorophenyl)-α-mercaptomethyl-benzene-propanamide melting at 142° C.

EXAMPLES 5 to 53

Using the procedure of Examples 1 and 2 or 3 and 4, α-(acetylthiomethyl-benzene-propanoyl chloride and the appropriate amine were reacted and then saponified to obtain the following products and the reaction conditions and physical constants are reported in the following Table.

Example 5: Ethanethioate of S-[3-(3,4-dimethoxyphenyl)-amino)-3-oxo-2-benzyl-propyl].
Example 6: N-(3,4-dimethoxyphenyl) α-mercaptomethyl-benzenepropanamide.
Example 7: Ethanethioate of S-[3-(2-benzothiazolylamino)-3-oxo-2-benzyl-propyl].
Example 8: N-(2-benzothiazolyl) α-(mercaptomethyl)-benzenepropanamide.
Example 9: Ethanethioate of S-[3-(2-aminophenylamino)-3-oxo-2-benzyl-propyl].
Example 10: N-(2-aminophenyl) α-(mercaptomethyl)-benzenepropanamide.
Example 11: Ethanethioate of S-[3-(3-aminophenylamino)-3-oxo-2-benzyl-propyl].
Example 12: N-(3-aminophenyl) α-(mercaptomethyl)-benzenepropanamide.
Example 13: Ethanethioate of S-[3-(4-aminophenylamino)-3-oxo-2-benzyl-propyl].
Example 14: N-(4-aminophenyl) α-(mercaptometyl)-benzenepropanamide.
Example 15: Ethanethioate of S-[3-(3-dimethylaminophenylamino)-3-oxo-2-benzyl-propyl].
Example 16: N-(3-dimethylaminophenyl) α-(mercaptomethyl)-benzenepropanamide.
Example 17: Ethanethioate of S-[3-(4-dimethylaminophenylamino)-3-oxo-2-benzyl-propyl].
Example 18: N-(4-dimethylaminophenyl) α-(mercaptomethyl)-benzenepropanamide.
Example 19: Ethanethioate of S-[3-(2-hydroxyphenylamino)-3-oxo-2-benzyl-propyl].
Example 20: N-(2-hydroxyphenyl) α-(mercaptomethyl)-benzenepropanamide.
Example 21: Ethanethioate of S-[3-(2,6-dimethylphenylamino)-3-oxo-2-benzyl-propyl]-
Example 22: N-(2,6-dimethylphenyl) α-(mercaptomethyl)-benzenepropanamide.
Example 23: Ethanethioate of S-[3-(4-hydroxyphenylamino)-3-oxo-2-benzyl-propyl].
Example 24: N-(4-hydroxyphenyl) α-(mercaptomethyl)-benzenepropanamide.
Example 25: Ethanethioate of S-[3-(3-hydroxyphenylamino)-3-oxo-2-benzyl-propyl].
Example 26: N-(3-hydroxyphenyl) α-(mercaptomethyl)-benzenepropanamide.
Example 27: Ethanethioate of S-[3-(2-chlorophenylamino)-3-oxo-2-benzyl-propyl].
Example 28: N-(2-chlorophenyl) α-(mercaptomethyl)-benzene-propanamide.
Example 29: Ethanethioate of S-[3-(4-pyridinylamino)-3-oxo-2-benzyl-propyl].
Example 30: N-(4-pyridinyl) α-(mercaptomethyl)-benzene-propanamide and its hydrochloride.
Example 31: Ethanethioate of S-[3-(3-chlorophenylamino)-3-oxo-2-benzyl-propyl].
Example 32: N-(3-chlorophenyl) α-(mercaptomethyl)-benzenepropanamide.
Example 33: Ethanethioate of S-[3-(2-thiazolylamino)-3-oxo-2-benzyl-propyl].
Example 34: N-(2-thiazolyl) α-(mercaptomethyl)-benzene-propanamide.
Example 35: Ethanethioate of S-[3-(4-methoxyphenylamino)-3-oxo-2-benzyl-propyl].
Example 36: N-(4-methoxyphenyl) α-(mercaptomethyl)-benzene-propanamide.
Example 37: Ethanethioate of S-[3-(3-methoxyphenylamino)-3-oxo-2-benzyl-propyl].
Example 38: N-(3-methoxyphenyl) α-(mercaptomethyl)-benzene-propanamide.
Example 39: Ethanethioate of S-[3-(2-methoxyphenylamino)-3-oxo-2-benzyl-propyl].
Example 40: N-(2-methoxyphenyl) α-(mercaptomethyl)-benzene-propanamide.
Example 41: Ethanethioate of S-[3-(3-pyridinylamino)-3-oxo-2-benzyl-propyl].
Example 42: N-(3-pyridinyl) α-(mercaptomethyl)-benzene-propanamide and its methane sulfonate.
Example 43: Ethanethioate of S-[3-(4-methoxycarbonylmethyl phenylamino)-3-oxo-2-benzyl-propyl].
Example 44: N-(4-methoxycarbonylmethylphenyl) α-(mercaptomethyl)-benzene-propanamide.
Example 45: Ethanethioate of S-[3-1H-benzimidazol-2-yl-amino)-3-oxo-2-benzyl-propyl].
Example 46: N-(1H-benzimidazol-2-yl) α-(mercaptomethyl)-benzene-propanamide and its methane sulfonate.
Example 47: Ethanethioate of S-[3-(4,5-dihydro-2-thiazolyl-amino)-3-oxo-2-benzyl-propyl].
Example 48: Ethanethioate of S-[3-(3-benzyloxyphenylamino)-3-oxo-propyl].
Example 49: N-(3-benzyloxyphenyl)-1-(mercaptomethyl)-acetamide..
Example 50: Ethanethioate of S-[3-phenylamino-3-oxo-2-methylpropyl].
Example 51: N-phenyl 2-(mercaptomethyl)-propanamide.
Example 52: Ethanethioate of S-[3-amino-3-oxo-2-benzyl-benzene-propanamide].
Example 53: α-(mercaptomethyl)-benzene-propanamide.

| Examples | R₁ | R₂ | R₃ | Solvent/ Saponification | Temp. in °C | Constants |
|---|---|---|---|---|---|---|
| 5 | CH₃CO | —CH₂-Φ | 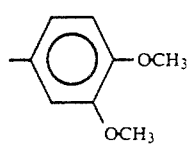 | CH₂Cl₂ | 0° C. | F = 102° C. |
| 6 | H | —CH₂-Φ | " | idem Ex. 2 | 0° C. | F = 131° C. |

-continued

| Examples | R₁ | R₂ | R₃ | Solvent/ Saponification | Temp. in °C. | Constants |
|---|---|---|---|---|---|---|
| 7 | CH₃CO | —CH₂-Φ | 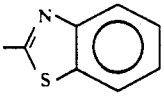 | CH₂Cl₂ | 0° C. | F = 50° C. |
| 8 | H | —CH₂-Φ | " | idem Ex. 2 | 0° C. | F = 149° C. |
| 9 | CH₃CO | —CH₂-Φ | 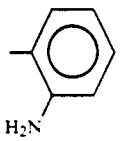 | CH₂Cl₂ | 0° C. | F = 119° C. |
| 10 | H | —CH₂-Φ | " | idem Ex. 2 | 0° C. | F = 136° C. |
| 11 | CH₃CO | —CH₂-Φ | 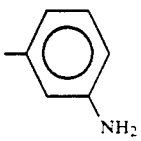 | CH₂Cl₂ | 0° C. | F = 97° C. |
| 12 | H | —CH₂-Φ | " | idem Ex. 2 | 0° C. | F = 122° C. |
| 13 | CH₃CO | —CH₂-Φ | 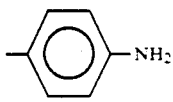 | CH₂Cl₂ | −10° C. | F = 128° C. |
| 14 | H | —CH₂-Φ | " | idem Ex. 2 | −5° C. | F = 138° C. |
| 15 | CH₃CO | —CH₂-Φ | 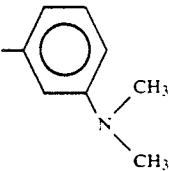 | CH₂Cl₂ | 0° C. | F = 120° C. |
| 16 | H | —CH₂-Φ | " | idem Ex. 2 | 0° C. | F = 98° C. |
| 17 | CH₃CO | —CH₂-Φ | 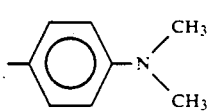 | CH₂Cl₂ | 0° C. | F = 115° C. |
| 18 | H | —CH₂-Φ | " | idem Ex. 2 | 0° C. | F = 124° C. |
| 19 | CH₃CO | —CH₂-Φ | 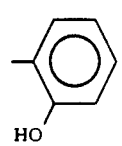 | CH₃COC₂H₅ | −5° C. | F = 88° C. |
| 20 | H | —CH₂-Φ | " | idem Ex. 2 | 0° C. | F = 84° C. |
| 21 | CH₃CO | —CH₂-Φ | 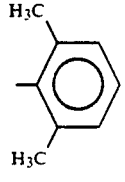 | CH₂Cl₂ | 0° C. | F = 120° C. |
| 22 | H | —CH₂-Φ | " | idem Ex. 2 | 0° C. | F = 160° C. |

-continued

| Examples | $R_1$ | $R_2$ | $R_3$ | Solvent/ Saponification | Temp. in °C | Constants |
|---|---|---|---|---|---|---|
| 23 | $CH_3CO$ | $-CH_2-\Phi$ | 4-hydroxyphenyl | $CH_3COC_2H_5$ | −5° C. | F = 120° C. |
| 24 | H | $-CH_2-\Phi$ | " | idem Ex. 2 | 0° C. | F = 50° C. |
| 25 | $CH_3CO$ | $-CH_2-\Phi$ | 3-hydroxyphenyl | $CHCl_3$ | 0° C. | F = 102° C. |
| 26 | H | $-CH_2-\Phi$ | " | idem Ex. 2 | 0° C. | F = 167-168° C. |
| 27 | $CH_3CO$ | $-CH_2-\Phi$ | 2-chlorophenyl | $CH_2Cl_2$ | 0° C. | F = 100° C. |
| 28 | H | $-CH_2-\Phi$ | " | idem Ex. 2 | 0° C. | F = 83° C. |
| 29 | $CH_3CO$ | $-CH_2-\Phi$ | 4-pyridyl | THF | 0° C. | F < 50° C. |
| 30 | H | $-CH_2-\Phi$ | 4-pyridyl·HCl | idem Ex. 2 $Et_2O/HCl$ | 0° C. | F = 167° C. |
| 31 | $CH_3CO$ | $-CH_2-\Phi$ | 3-chlorophenyl | $CH_2Cl_2$ | 0° C. | F = 113° C. |
| 32 | H | $-CH_2-\Phi$ | " | idem Ex. 2 | 0° C. | F = 121° C. |
| 33 | $CH_3CO$ | $-CH_2-\Phi$ | thiazolyl | $CH_2Cl_2$ | 0° C. | F = 103° C. |
| 34 | H | $-CH_2-\Phi$ | " | idem Ex. 2 | 0° C. | F = 90° C. |
| 35 | $CH_3CO$ | $-CH_2-\Phi$ | 4-methoxyphenyl | $CH_2Cl_2$ | 0° C. | F = 118° C. |
| 36 | H | $-CH_2-\Phi$ | " | idem Ex. 2 | 0° C. | F = 115° C. |
| 37 | $CH_3CO$ | $-CH_2\Phi$ | 3-methoxyphenyl | $CH_2Cl_2$ | 0° C. | F = 115° C. |
| 38 | H | $-CH_2-\Phi$ | " | idem Ex. 2 | 0° C. | F = 72-73° C. |

-continued

| Examples | $R_1$ | $R_2$ | $R_3$ | Solvent/ Saponification | Temp. in °C | Constants |
|---|---|---|---|---|---|---|
| 39 | $CH_3CO$ | $-CH_2-\Phi$ | 2-methoxyphenyl ($H_3CO$ substituent) | $CH_2Cl_2$ | 0° C. | — |
| 40 | H | $-CH_2-\Phi$ | " | idem Ex. 2 | -5° C. | F ≈ 50° C. |
| 41 | $CH_3CO$ | $-CH_2-\Phi$ | 4-methylpyridinyl | $CH_2Cl_2$ | 0° C. | F = 124–125° C. |
| 42 | H | $-CH_2-\Phi$ | 4-methylpyridinyl et son sel de $CH_3SO_3H$ | idem Ex. 2 $CH_3SO_3H/Et_2O$ | 0° C. 0, -5° C. | F = 103–104° C. F = 146° C. |
| 43 | $CH_3CO$ | $-CH_2-\Phi$ | $-\Phi-CH_2-CO_2CH_3$ | $CH_2Cl - O\!\!\diagdown\!\!N-CH_3$ (morpholine) | -10° C. | — |
| 44 | H | $-CH_2-\Phi$ | " | idem Ex. 2 | 0° C. | F = 98° C. |
| 45 | $CH_3CO$ | $-CH_2-\Phi$ | 2-methylbenzimidazolyl | THF | 0° C. | F = 70–75° C. |
| 46 | H | $-CH_2-\Phi$ | 2-methylbenzimidazolyl · $CH_3SO_3H$ | idem Ex. 2 $CH_3SO_3H/Et_2O$ | 0° C. -9° C. | F = 142° C. |
| 47 | $CH_3CO$ | $-CH_2-\Phi$ | 2-methylthiazolyl | $CH_2Cl_2$ | -10° C. | F = 114° C. |
| 48 | $CH_3CO$ | H | 3-($O-CH_2-\Phi$)phenyl | $CH_2Cl_2$ | -7° C. | F = +87° C. |
| 49 | H | H | " | idem Ex. 2 | -10° C. | F = +99° C. |
| 50 | $CH_3CO$ | $CH_3$ | phenyl | $CH_2Cl_2$ | -10° C. | F = 106° C. |
| 51 | H | $CH_3$ | " | idem Ex. 2 | 0° C. | F = 100° C. |
| 52 | $CH_3CO$ | $-CH_2-\Phi$ | H | $CH_2Cl_2$ | 0° C. | F = 78° C. |
| 53 | H | $-CH_2-\Phi$ | H | idem Ex. 2 | 0° C. | F = 69° C. |

EXAMPLE 43A

Methyl (4-amino-phenyl)-acetate hydrochloride which was the starting material for Example 43 was prepared by bubbling gaseous hydrogen chloride through a mixture of 25.26 g of (4-amino-phenyl)-acetic acid and 200 ml of methanol and the mixture was refluxed for one hour and cooled to 20° C. The solvent was evaporated at 45° C. and the residue was triturated with ether and dried to obtain 32.2 g of the desired product melting at ≈165° C.

EXAMPLE 54

Tablets were prepared containing 50 mg of the product of Example 1 or Example 38 or 200 mg of the product of Example 2 and sufficient excipient of lactose, starch, talc and magnesium stearate for a final tablet weight of 350 mg.

PHARMACOLOGICAL DATA

A. Inhibition of Enkephalinase

Enkephalinase activity was determined in a striatum membrane fraction of rats. The striatum was placed in ice and was homogenized in buffered 0.05M Tris with a pH of 7.4 (20 times the volume) and after a first centrifugation at 1000 g, the particular fraction obtained was subjected to two centrifugations for 10 minutes at 20,000 g. The culot was then suspended in buffered Tris and kept at 4° C. The amount of proteins was determined by the Comassie blue method.

After preincubation at 25° C. for 15 minutes, an aliquot of proteins was incubated at 25° C. for 15 minutes in the presence of 20 nanomole of tritiated leucine-enkephaline (against the first amino acid) previously purified, of 1 mM of puromycin and the test product in buffered Tris. The hydrolysis reaction was stopped by addition of 0.2N hydrochloric acid and the incubate was subjected to a deproteinization by heating at 95° C. for 15 minutes. Under these conditions, the kinetic reaction was linear. The tritiated metabolites obtained by hydrolysis were separated from enkephaline by chromatography over a column of porapak Q and elution with buffered Tris whereby enkephaline was retained in the column and was released in the following ethanolic phase. The activity of the different products was expressed in 50% inhibitory concentration called $CI_{50}$ in Table II.

TABLE II

| Product of Examples | Enkaphalinase inhibition $CI_{50}$ in $10^{-6}M$ |
| --- | --- |
| 1 | 10 |
| 2 | 1 |
| 3 | 1 |
| 4 | 1 |
| 30 | 0.1 |
| 36 | 0.05 |
| 38 | 0.06 |

B. Analgesic Activity

The test was a variation of the Randall et al test [Arch. Int. Pharmacodyn. Vol. III (1957), p. 409] wherein the analgesic activity was determined in rats by the threshold of sensitivity to pain lowered by an inflammation. The inflammation was obtained by injection of 0.25 mg of carraghenin in the plantary aponevrose of a rear paw and pain was provoked by a mechanical pressure applied to the right face of the paw and was increased regularly by an analgesimeter. The pain thresold was appreciated by the pressure necessary to release a reaction by withdrawing the paw or a vocal reaction from the animals. The test products were administered orally four hours after the injection of carraghenin and the pain threshold was measured immediately before the injection of irritant and one hour after treatment. The results are reported in Table III.

TABLE III

| Product of Example | DA in mg/kg |
| --- | --- |
| 1 | 20 |
| 2 | 4 |
| 4 | 50 |
| 30 | 4 < DA < 20 |

Various modifications the produdts and processes of the invention may be made without departing from the spirit or scope thereof and it is to be understood that the invention is to be limited only as defined in the appended claims.

What we claim is:

1. A method of relieving pain in warm-blooded animals comprising administering to warm-blooded animals an analgesically effective amount of at least one compound selected from the group consisting of amides of the formula

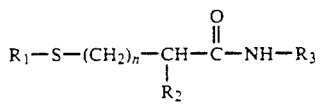

wherein $R_1$ is selected from the group consisting of hydrogen and

$R_1$ is selected from the group consisting of alkyl of 1 to 5 carbon atoms and aryl optionally substituted with at least one member of the group consisting of —OH, alkyl and alkoxy of 1 to 5 carbon atoms, —NO₂ and halogen, n is an integer from 1 to 5, $R_2$ is selected from the group consisting of hydrogen, aryl and aralkyl of 6 to 15 carbon atoms optionally substituted with at least one member of the group consisting of alkyl and alkoxy of 1 to 5 carbon atoms, —OH, halogen, and —CF₃, $R_3$ is phenyl optionally substituted with at least one member of the group consisting of alkyl and alkoxy of 1 to 5 carbon atoms, —OH, —NO₂, halogen, —CF₃, carboxymethyl, alkoxycarbonylmethyl with 1 to 5 carbon atoms, aralkoxy of 7 to 15 carbon atoms and

X and X' are individually selected from the group consisting of hydrogen and alkyl of 1 to 5 carbon atoms and their salts with non-toxic, pharmaceutically acceptable acids and bases.

2. A method of claim 1 wherein in the compound $R_1$ is acetyl.

3. A method of claim 1 wherein in the compound n is 1 and $R_2$ is benzyl.

4. A method of claim 1 wherein in the compound $R_3$ is phenyl optionally substituted with at least one member of the group consisting of chlorine and methoxy.

5. A method of claim 1 wherein the active compound is selected from the group consisting of α-(mercaptomethyl)-N-phenyl-benzene-propanamide, ethanethioate of S-[3-oxo-3-phenylamino-2-benzyl-propyl], α-(mercaptomethyl)-N-(3-methoxyphenyl)-benzene-propanamide, α-(mercaptomethyl)-N-(4-methoxyphenyl)-benzene-propanamide, and their salts with non-toxic, pharmaceutically acceptable acids and bases.

* * * * *